(12) United States Patent
Shulov et al.

(10) Patent No.: US 6,555,109 B1
(45) Date of Patent: Apr. 29, 2003

(54) ANALGESIC FROM SNAKE VENOM

(75) Inventors: Abaron Shulov, deceased, late of Mevaseret Zion (IL), by Jocheved Shulov, heiress; Naftali Primor, Rehovot (IL)

(73) Assignee: S.I.S. Shulov Institute for Science Ltd., Rehovot (IL)

(*) Notice: Subject to any disclaimer, the term of this patent is extended or adjusted under 35 U.S.C. 154(b) by 0 days.

(21) Appl. No.: 09/600,498

(22) PCT Filed: Jan. 13, 1999

(86) PCT No.: PCT/IL99/00020

§ 371 (c)(1),
(2), (4) Date: Nov. 2, 2000

(87) PCT Pub. No.: WO99/36078

PCT Pub. Date: Jul. 22, 1999

(51) Int. Cl.$^7$ ............. A61K 38/46; A61K 39/395; C07K 16/00; C07K 1/00
(52) U.S. Cl. ............. 424/94.67; 424/172.1; 530/387.1; 530/389.1; 530/856; 530/858
(58) Field of Search ............. 424/94.67, 85.8, 424/172.1; 530/387.1, 389.1, 856, 858

(56) References Cited

U.S. PATENT DOCUMENTS

| 5,164,196 A | 11/1992 | Plata et al. ............. 424/548 |
| 5,196,193 A | * 3/1993 | Carroll |

FOREIGN PATENT DOCUMENTS

| SU | 435824 | 6/1975 |
| WO | WO 8605399 | * 9/1986 |
| WO | WO 91/01740 | 2/1991 |

OTHER PUBLICATIONS

Djaldetti, M. et al., "Ultrastructural Alterations of Peripheral blood Cells Due to Vipera Palaestinae Snake Bite," *Toxicon*, vol. 15, pp. 379–384, (1977).
Russell, F.E., "The Use of Venoms and Venom Fractions in Medicine and Biology," Toxicon, vol. 15, pp. 267–268, (1977).
Rosenberg, Philip, ed., *Toxicon, Official Journal of the International Society on Toxinology*, vol. 15, (1977).
Xiong, Y., et al., "Using snake venon to substitute for addictive drugs," *Toxicon*, vol. 30, No. 5/6, pp. 567–568, (1992).
Pu, X.C. et al.; "A Novel Analgesic Toxin (Hannalgesin) from the Venom of King Cobra (Ophiophagus Hannah)"; *Toxicon*, vol. 33, No. 11; pp. 1425–1430, (1995).
Giorgi, R. et al.; "Analgesic Effect Evoked by Low Molecular Weight Substances Extracted from *Crotalus Durissus Terrificus* Venom"; *Toxicon*, vol. 31, No. 10; pp. 1257–1265, (1993).
Dutta, A.S. et al.; "Neuropharmacological studies on the venom of *Vipera russelli*"; *Indian J. of Exp. Biol.*; vol. 29; pp. 937–942; (Oct. 1991).
Bevan, P. et al.; "Receptor–Active Protein from Russell's Viper (*Viper Russelli Russelli*) Venom"; *J. of Biol. Chem.*, vol. 258, No. 6, pp. 5319–5326, (1983).

* cited by examiner

Primary Examiner—Christopher R. Tate
Assistant Examiner—Randall Winston
(74) Attorney, Agent, or Firm—Gary M. Nath; Todd L. Juneau; Joshua B. Goldberg

(57) ABSTRACT

A substantially non-toxic fraction isolated from the venom of *Vipera xanthina* is disclosed which fraction has an analgesic effect. The fraction is preferably purified on an ion exchange column from *Vipera xanthina palestinae*. Also described are a pharmaceutical composition for use as an analgesic comprising the non-toxic fraction, and a method for the relief of pain comprising administrating the non-toxic fraction.

17 Claims, 2 Drawing Sheets

ANALGESIC FROM SNAKE VENOM

FIELD OF THE INVENTION

The present invention relates to the use of snake venom as an analgesic.

BACKGROUND OF THE INVENTION

Although pain is a crucially important physiological response, it also results in unnecessary suffering and agony. The control and relief of pain is an important branch of medicine. Pain may come about both as a result of disease as well as a result of medical treatment such as chemotherapy. In either case, it is important to alleviate the pain as much as possible so as to enable the sufferer to function normally.

Two neural pathways relating to pain act concurrently in the body: (1) a sensory pathway which senses tissue damage and subsequently produces a feeling of pain; (2) an analgesic pathway which reduces the feeling of pain and prevents the flow of information about the pain to the central nervous system (CNS), thus allowing the organism to maintain it's normal activity in spite of an injury. Anesthesia can be realized either by use of a drug which inhibits peripheral nerves that act as pain sensors or by enhancement of the natural analgesic system. Since these are different pathways, they are affected by different substances. For example, aspirin and lidocaine are active on the peripheral sensory pathway, while morphine and related substances are active on the analgesic system.

The most efficient analgesics currently in use are morphine-related substances of opiatic origin. It's well known that the brain makes a variety of endogenic opiates, and this explains the powerful effect of these substances. Their action on neurons is mediated by specialized receptors. Signals regulated by these receptors prevent the flow of information from the peripheral pain neurons to the CNS. These CNS neurons are also sensitive to a variety of other chemical substances including catecholamines (serotonin, noradrenalin etc.), neuroactive peptides (neurotensin) and inhibitory amino acids (glycin and GABA).

Out of some 4000 currently living species of snakes, approximately 400 species are known to be venomous. The venomous species are classified into five families, one of which is the Viperidae family, commonly known as vipers. Snakes of the Viperidae are distributed in Europe, Asia and Africa, and comprise 8 genera, one of which is the genus Vipera. The genus Vipera comprises the following species: *V. berus; V. lebatina; V. russelii; V. superciliaris; V. ursinii; V. aspis; V. latifii; V. bornmulleri; V. ammodytes; V. xanthina;* and *V. mauritanica.* The species *V. xanthina* has been further classified into three sub-species: *V. xanthina raddei, V. xanthina xanthina,* which is found generally in southern Europe, and *V. xanthina palestinae* which is found in Israel.

Snake venom comprises a large variety of different substances. Out of several hundreds of estimated compounds, it is believed that only 4–8 are involved in the toxic effect of the venom. Despite functional similarity, snake venoms differ considerably in their chemical composition. Each species possesses it's own characteristic venom composition. To date, only a few hundred compounds from some 400 venomous snake species have been characterized. These include enzymes, toxins, growth factors, etc. Most of the isolated venom compounds are of unknown function.

Traditionally, snake venom is considered a source of toxic substances. However, it is also a source of analgesics. Doctors who treated patients bitten by a South American snake (*Crotalus durissus terrificus*) reported that although these patients were in a life-threatening condition, they felt no pain. A neurotoxin product isolated from snake venom was regarded as a new type of analgesic at the First Congress of Neurotoxicology (1977) in Yugoslavia. These and other observations lead to attempts to isolate anesthetic compounds from snake venom.

Bevan, P. and Hiestand, P. (1983) *J. Biol. Chem.* 258:5319–5326 describe a single chain polypeptide isolated from *Vipera russelli russelli* venom by cation exchange chromatography. The polypeptide competes with the binding of monoamines and opiate ligands to their respective receptors, and injection of the polypeptide intracerebroventricularly in rats causes marked sedation. The authors state that the polypeptide is a large and highly charged molecule which is unlikely to pass the blood-brain barrier. The polypeptide was found to be a moderately potent toxin, similar to the crude venom.

Dutta, A. S. and Chaudhuri, A. K. N. (1991) *Indian J. Exp. Biol.* 29:937–942 describe experiments carried out with crude venom of *Vipera russelli* on mice and rats. The venom was injected intraperitoneally and intravenously, and was found to produce alterations in general behavior patterns connected with the CNS. The venom showed significant analgesic activity in one assay, but no activity in two other assays.

WO 91/01740 published Feb. 21, 1991 discloses the use of lyophilized *Crotalus atrox* whole venom in a pharmaceutical composition for external use. The composition has analgesic, hyperaemizating and spasmolysant activity.

Giorgi, R., Bernardi, M. M. and Cury, Y. (1993) *Toxicon* 31:1257–1265 describe analgesic effects evoked by low molecular weight substances extracted from *Crotalus durissus terrificus* venom by ultrafiltration. The extract was administered to mice subcutaneously, intraperitoneally and orally.

CN 1,072,344 published May 26, 1993 discloses a snake toxin ointment containing a commercial snake toxin enzyme (source not given), a leukocyte peptide factor and Bingpian, a known Chinese analgesic medicine. The ointment functions as an antibiotic with no toxicity or side effects.

Pu, X. C., Wong, P. T. H. and Gopalakrishnakone, P. (1995) *Toxicon* 33:1425–1431 describes a neurotoxin purified from king cobra venom by gel filtration and HPLC. The toxin was administered i.p., p.o. or i.c.v. to mice and found to have a potent analgesic effect.

U.S.S.R. Patent No. 435,824 describes an analgesic composition prepared from Nayaksin dry cobra venom. This snake is from the Naja species which belongs to the Elapidae family.

For over 20 years, an ointment named Viprosalum or Viprosal has been available in the former Soviet Union and in Eastern Europe for the relief of pain. This ointment is a mixture of a viper venom (European species) dissolved in Vaseline together with Lanolin, camphor and solicitate.

SUMMARY OF THE INVENTION

It is an object of the present invention to provide an analgesic substance isolated from snake venom which is substantially non-toxic.

According to one aspect of the present invention, there is provided a substantially non-toxic fraction isolated from the venom of *Vipera xanthina,* the fraction having an analgesic effect.

Further in accordance with this aspect of the present invention, there is provided a pharmaceutical composition for use as an analgesic comprising a substantially non-toxic fraction isolated from the venom of *Vipera xanthina.*

In a preferred embodiment of the present invention, the pharmaceutical composition is for topical use.

Although all of the experiments described below which illustrate the invention involve the sub-species *Vipera xanthina palestinae* (hereinafter *V. palestinae*). It is to be understood that this sub-species serves only as an example for the entire species *Vipera xanthina.* As stated above, each venomous species possesses it's own characteristic venom composition.

The fraction provided by the invention combines a number of properties previously unreported as appearing together in the same material. These properties include: (1) derivation from *Vipera xanthina* venom; (2) possession of analgesic activity; (3) substantially no toxicity; (4) substantially purified; and (5) active when administered topically. This substance has been named "Zephalin".

In the present specification, the term non-toxic is defined as the non-occurrence of pathological phenomena as a result of using pharmacological levels of Zephalin which have an analgesic effect. The term substantially non-toxic is defined as including acceptably low toxicity as well as non-toxicity.

Although Zephalin is a purified fraction of the crude venom, it apparently comprises more than one substance. The present invention includes not only Zephalin but also various products which may be purified from Zephalin and which possess the properties of Zephalin. The invention also includes derivatives of these products, which retain the properties of Zephalin. In the case of proteinaceous material, such derivatives would include proteins or polypeptides in which one or more amino acids have been added, deleted and/or replaced. Other chemical modifications are also contemplated.

Zephalin may be used to prepare a pharmaceutical composition for use as an analgesic. Such a composition would also comprise a pharmaceutically acceptable carrier or excipient such as a mixture of Lanolin and Vaseline. The composition may be prepared for parenteral use, for example in a saline solution, or for topical use in an ointment, cream or salve. In order to afford relief to a subject suffering from pain, the pharmaceutical composition would either be injected or applied topically at an appropriate location. Other possible modes of application would be oral and rectal. Any pharmaceutical composition would generally include a pharmaceutically acceptable carrier or excipient in addition to the active ingredient. As Zephalin sometimes acts after a lag period, it is to be expected that it will be especially effective with respect to chronic pain, although it may be used to treat any type of pain.

BRIEF DESCRIPTION OF THE DRAWINGS

The present invention will be better understood from the following detailed description of preferred embodiments, taken in conjunction with the following drawings in which.

DETAILED DESCRIPTION OF PREFERRED EMBODIMENTS

Materials and Methods

*Vipera palestinae* venom was obtained by milking several hundred snakes. Their venom was frozen and lyophilized.

A. Analgesic assay

In each test, a few tens of hamsters of similar weight and age were used. The hamsters were divided into groups according to the number of samples to be tested. Ointment (50% Lanolin and 50% Vaseline) containing the tested substance was applied to the animal's fur on the back region. The fur was not removed so as to ensure that no damage to the skin occurred. A control group of hamsters was treated with ointment without Zephalin. Hamsters were treated by topical application for 6, 14 or 21 consecutive days. The test for analgesity was conducted on the day following the last application of the ointment.

In a typical test, a constant amount of ointment with or without an analgesic substance is applied to each animal for a predetermined period of days. Following this period, pain is induced by a subcutaneous injection of 0.8 ml of 1N HCl/0.1 kg body weight in the femur region. The hamsters respond to the HCl injection by touching the area of injection with the tongue, this being called a "lick". 20 minutes after injection the hamster is observed for 40 min and the number of "licks" are counted. The number of "licks" serves as a quantitative indication of the HCl induced pain.

The analgesic effect is determined by comparing the mean number of "licks" in control animals to the number in treated animals. The significance of the difference was determined using t-test statistics.

B. Lethal Dose determination

Four different concentrations of the tested substance were injected into the peritoneum of mice weighing 20–25 grams. Eight mice were injected with each concentration. The method of calculating the dose of the tested substance leading to 50% mortality ($LD_{50}$) is as described in Reed, L. J. and Muench, H. (1938) Am. J. Hygiene 27:493. An $LD_{50}$ unit is defined as the amount of tested substance necessary to cause the death of 50% of the injected mice per 20 g body weight (mg/20 g).

C. Toxicity determinations

Hamsters were used for short-term determinations (up to 10 days), in which the tested material was injected into the peritoneum for 10 days. Rats were used for long term determinations during which ointment was topically applied once a day, 6 days a week, over a period of 4 months (100 applications total).

D. Protein determination

The amount of proteinaceous material in Zephalin and its concentration in each separation were determined spectroscopically at 280 nm using an ovalbumin standard of a known concentration.

EXAMPLES

I. Purification of Zephalin

Figure 1:
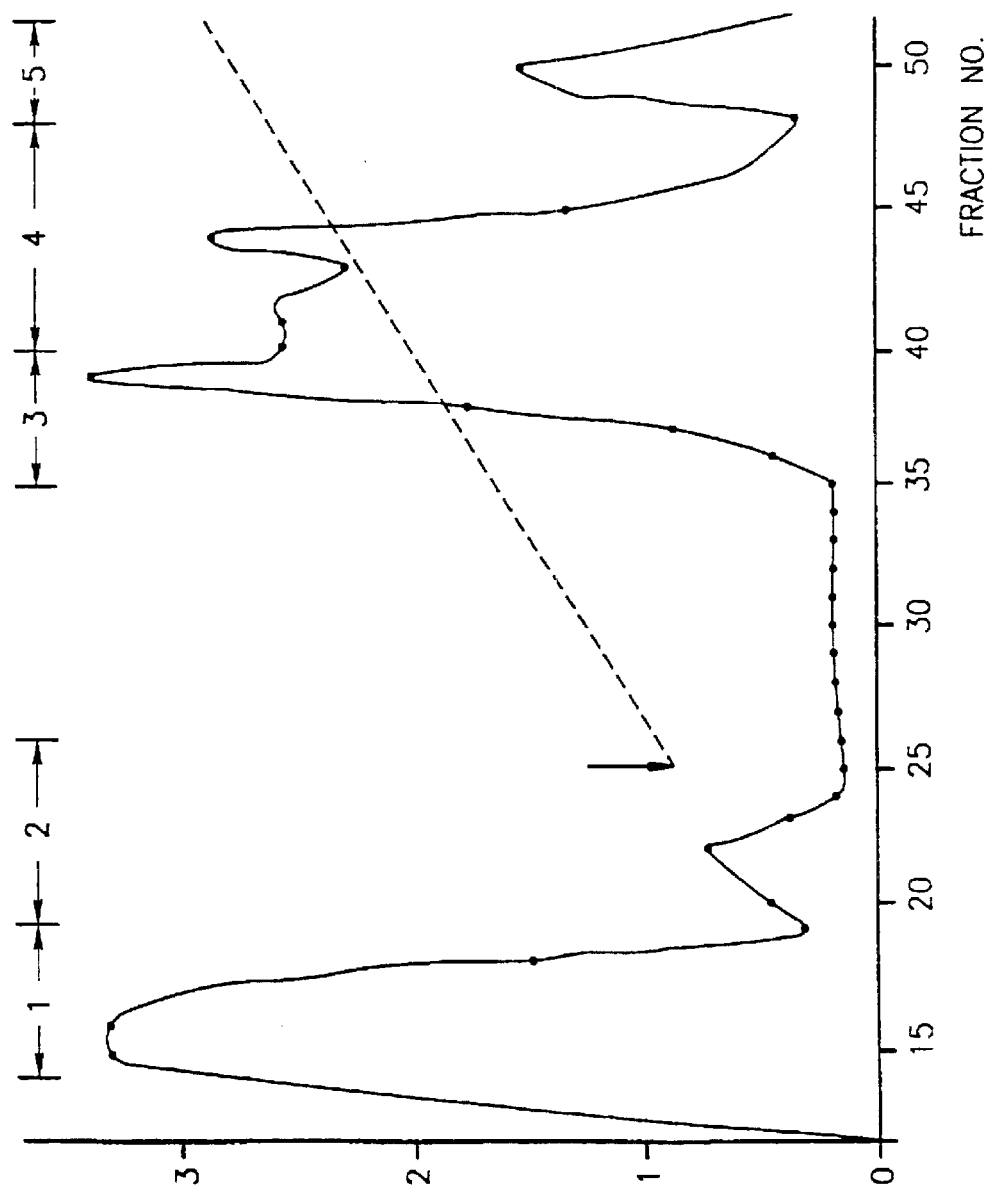
FIG. 1 is a graph showing the UV absorbency at a wavelength of 280 nm of column fractions eluted from a QAE Sephadex column on which *Vipera palestinae* venom was loaded.

In a typical purification, 0.4 gr. of whole *Vipera palestinae* venom were dissolved in ammonium acetate buffer (0.05M pH 8.0) and applied to a QAE Sephadex (Pharmacia) ion exchange column (1.3×50 cm) which was equilibrated with the above buffer. The elution fractions were collected in 5 ml tubes (see FIG. 1). Protein content of the fractions was followed by measuring the optical density of the fractions at 280 nm. Following the elution of the second protein peak, a gradient of 2 M of ammonium acetate was applied which resulted in the elution of more $A_{280}$ absorbing fractions. Five groups of $A_{280}$-absorbing fractions were pooled and all the five fraction pools were tested for toxicity in mice and analgesic activity (see below).

Figure 2A:
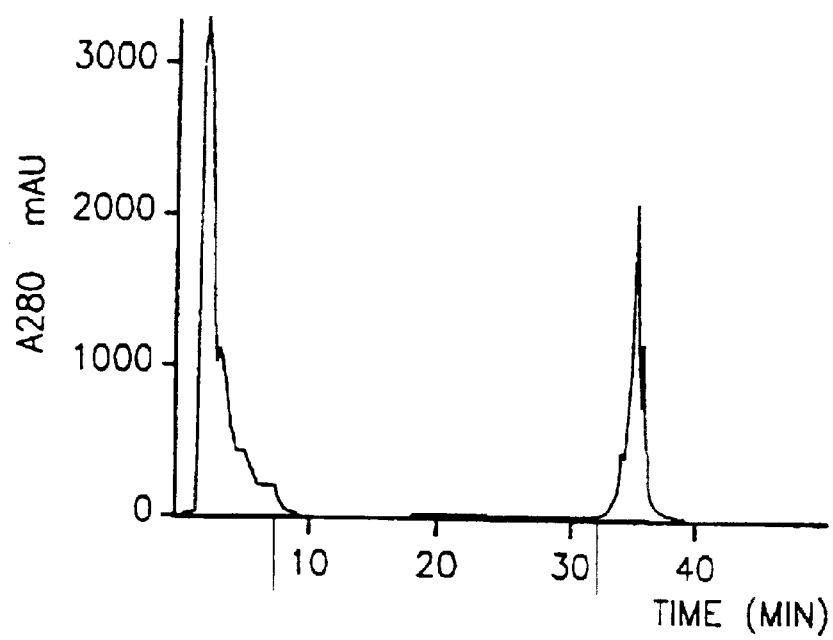
FIGS. 2A and B are graphs illustrating the results obtained during purification of Zephalin on a Mono Q column. The Y-axis represents the UV absorbency at 280 nm and the X-axis is the elution time in minutes. Graph B is an enlargement of graph A in the region of 9–31 minutes, and at a lower range of absorbencies.
Figure 2B:
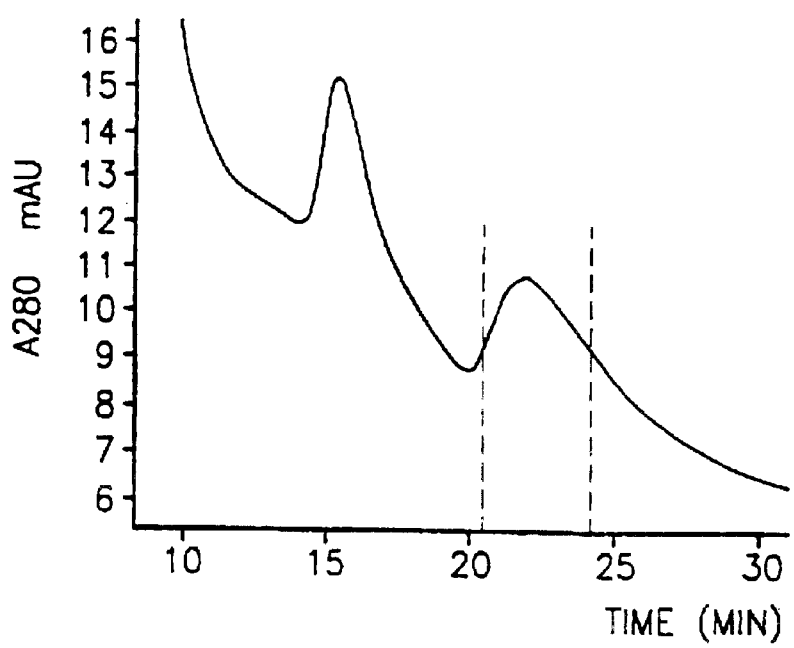

In a preferred isolation method, the QAE column is replaced by an FPLC Mono Q column (Pharmacia). In a typical experiment, 50–80 mg of *V. palestinae* venom were dissolved in 20 mM Tris buffer, pH 7.5, at a final concentration of 0.1 g/ml. Following centrifugation and the removal of the precipitate, the supernatant was filtered through a microfilter (40 micron) and 0.1–0.2 ml were applied to a 1×10 cm Mono Q column. The A solvent consisted of 20 mM Tris buffer pH 7.5 and the B buffer consisted of 20 mM Tris and 0.5M NaCl. Buffer A alone was used during the first 20 min of elution. During the following 45 min, a mixture of buffers A and B (50%:50%) was used and for the last 5 min, 100% buffer B was used. Zephalin eluted in the region of 20–25 min (see FIG. 2B), as determined by various assays (see below). The elution can also be carried out using buffer A alone, which may be replaced by 20 mM ammonium acetate. Thirty purifications using the Mono Q column were carried out over a period of 18 months, all giving similar results.

II. Characterization of Zephalin

A. Determining the analgesic fraction pool

In this preliminary test, a very high concentration of each of fraction pools 1–5 (from the QAE Sephadex column, see I above) was used in order to identify the pool containing analgesic activity. Therefore, the analgesic activity was detected after only 6 days of application. Lyophilized material taken from each of fraction pools 1–5 was dissolved in an ointment composed of 50% Lanolin and 50% Vaseline at a concentration of 2 mg/g. 0.2 gr. of this ointment were applied daily over a period of 6 days to a group of 10 hamsters over an area of 2–3 cm² of fur, as described in the Methods section above. Protein, toxicity and analgesic activity for each pool were determined as described above. The results are summarized in Table 1.

TABLE 1

| Pool number | Analgesic effect Number of licks (average + S.D.) | Toxicity No. of $LD_{50}$ units (mg/20 g) | Protein (mg*) |
| --- | --- | --- | --- |
| 1 | 11.1 + 6.1 (0.0004) | 2880 | 86.4 |
| 2 | 11.2 + 7.7 (0.003) | 7.9 | 9.5 |
| 3 | 60.3 + 27.5 (0.8) | 228 | 68.5 |
| 4 | 31.8 + 14.9 (0.09) | 84 | 75.6 |
| 5 | 49.7 + 36.1 (0.7) | 0 | 20.0 |
| Control | 45.2 + 30.7 | — | 0 |

*Protein was determined by the Lowry method using an ovalbumin standard.

The numbers in parenthesis signify probability values (p) obtained by t-test in comparison to control.

The analgesic activity was concentrated in pools 1 and 2. Pool 2 contained about 11% of the protein but only 0.002% of the toxicity. Pool 2 had the lowest toxicity between the two analgesic pools and the lowest amount of protein among all the pools. Fraction pool 2 was therefore used in further experiments as Zephalin. These findings indicate that the toxicity and analgesic activity reside in different venom components, and that Zephalin is substantially non-toxic (see also below).

The Zephalin prepared with the Mono Q column is completely separated from the toxic components of the venom, as discussed in Section IV.A1 below.

In subsequently described studies, the Zephalin used is that prepared by the QAE column, unless otherwise indicated.

B. The nature of Zephalin

In order to determine the nature of Zephalin, 0.1 mg of Zephalin prepared on a Mono Q column were dissolved in the solution buffer. In parallel, pronase E was prepared by dissolving 2.4 mg of pronase E in elution buffer (20 mM tris, pH 7.5). Three tubes were prepared, one containing the protease only, a second containing Zephalin only, and a third in which Zephalin was incubated with 5 µl of pronase E (0.17 micrograms). The tubes were incubated for 24 hr at room temperature, and then tested for analgesic activity.

The result was that only tube 2 had analgesic activity. This test was repeated 3 times with identical results. It can therefore be concluded that Zephalin is of a proteinaceous nature or a protein is required for it's analgesic activity.

C. Purity of Zephalin

The 20–25 min. fraction from the Mono Q column (see I above) contained 0.02±0.05 S.D. mg/ml protein, based on 10 separation runs. Each run resulted in a yield of 0.1 mg of Zephalin. This amount correspondents to 0.6% of the total venom protein applied to the column. This indicates the high purity of Zephalin.

III. Analgesic Activity

The analgesic activity of Zephalin was tested using preparations prepared over a period of two years. 0.2 ml of the Zephalin fraction containing 0.01 mg protein was dissolved in 50 gr of ointment resulting in a concentration of 0.0002 mg Zephalin/g ointment. Hamsters were topically treated with the ointment as described in the Methods section for 21 days. The results are summarized in Table 2.

TABLE 2

| Date of experiment | May 1991 | June 1991 | December 1991 | May 1992 | April 1993 | May 1993 | September 1993 |
|---|---|---|---|---|---|---|---|
| Sample* | 3 ± 3 | 11 ± 15 | 8 ± 7 | 2 ± 4 | 17 ± 22 | 8 ± 5 | 16 ± 11 |
| Control* | 85 ± 29 | 44 ± 11 | 55 ± 28 | 16 ± 9 | 58 ± 45 | 49 ± 42 | 41 ± 34 |
| p | 0.000 | 0.0009 | .0000 | .0009 | 0.0142 | .0008 | 0.028 |

*- average number of "licks" from 7 experimnents ± S.D.

These experiments show that the Zephalin treated hamsters had reduced sensation to the HCl induced pain as compared to the control.

IV. Toxicological Studies

A. Injection of Zephalin

A1. Mice (20–25 gr each) were injected s.c. with an amount of 0.05 mg of Zephalin prepared using the Mono Q column. This amount is 250 times the amount necessary to produce an analgesic effect in hamsters. At this dose, Zephalin was not toxic to the mice, and no visible symptoms were observed. In contrast, injection of 0.02 mg of the first fractions (tubes 2–7) eluted from the column caused immediate death of all 5 mice injected. This finding demonstrates the substantial non-toxicity of the analgesic fraction.

A2. In a further experiment, 3 groups of 8 hamsters (100–120 grams) each were injected. Lyophilized Zephalin was dissolved in a physiological saline solution at a concentration of 0.002 mg/ml and 0.1 ml or 0.2 ml were injected daily for 10 days into the peritoneum of the first and second groups, respectively. The third (control) group was injected with 0.2 ml of saline only. Following the 10 days of injections, blood was taken for the testing of biochemical parameters and histopathological tests.

Among the biochemical factors tested, an increase in cholesterol and amylase were observed in the first two groups (results not shown). However no significant changes were observed in the function of liver enzymes (LDH, SGOT, SGPT).

A3. The histopathology of the experimental animals of Section A2 was investigated. No significant histopathological differences were detected between the groups injected with Zephalin and the control group.

B. Topical treatment

Zephalin was prepared in ointment as described in the Methods section (analgesic assay). Three groups of 10 rats each (males and females) in a weight range of 120–140 g were used. The ointment was topically applied as described in the Methods section. The ointment applied to groups 1 and 2 comprised Zephalin at a concentration of 0.0002 and 0.001 mg/g, respectively. In group 3, the ointment comprised solvent alone as a control. 0.2 g of ointment were applied daily to each rat. During the four months of the experiment, each rat of group 1 received a total of 0.03 mg/kg body weight and each rat of group 2 received 0.15 mg/kg body weight. During the experiment, no changes in the rats' behavior or body weight were observed.

Blood and urine were collected in the laboratory. For collecting of urine, the animals were placed on a plastic surface, the urine collected and immediately tested using Multistick. For the taking of blood the rats were anesthetized and arterial blood taken. The plasma was removed by centrifugation, stored at 4° C. and tested for biochemical parameters.

B1. It was found that Zephalin caused a significant increase in the following blood enzyme levels: alanine aminotransferase (SGPT), aspartate aminotransferase (SGOT) and lactate dehydrogenase (LDH). However, when the experiment was repeated using the more purified Mono Q fraction, no increase in SGPT or SGOT was detected. No significant differences with the control group were detected in the following blood analyte levels: Cre; $Ca^{2-}$; P(i); Glu; Ur; Chl; TP; Alb; Bili; Al.Phos; AMY (results not shown).

B2. The results of the measurement of various biochemical parameters in urine are summarized in Table 3:

TABLE 3

| | Glucose | Biliriubin | Ketone | Specific Activity | Blood Non-hemolyzed | pH | Protein | Uro-binogen | Nitrate | Leukocytes |
|---|---|---|---|---|---|---|---|---|---|---|
| Control (8 rats) | (−) | (+)1 (−)7 | (−) | 1.014 | (0)1 | 7.6 | (0)2 (−)6 | 0.2 | (+)1 (−)7 | (0)1 (−)7 |
| Zephalin[1] 0.001 mg/gr (9 rats[3]) | (−) | (+)1 (−)8 | (0)3 (−)6 | 1.004 | (0)4 (−)5 | 8.0 | (0)3 (−)6 | 0.2 | (−) | (0)1 (−8) |
| Zephalin[1] 0.0002 mg/gr (6 rats[3]) | (−) | (−) | (0)1 (−)5 | 1.006 | (0)5 (−)1 | 7.9 | (6)4 (−)2 | 0.2 | (+)2 (−)4 | (0)3 (−)3 |
| Zephalin[2] 0.0002 mg/gr (11 rats[4]) | (−) | (−) | (0)5 (−)6 | 1.014 | (0)2 (−)9 | 6.9 | (+ +)1 (0)2 (−)8 | 0.2 | (−) | (−) |

[1]. Purified on QAE Sephadex column
[2]. Purified on Mono Q column
[3]. Male and female rats used
[4]. Only male rats used

TABLE 3-continued

|  | Glucose | Biliriubin | Ketone | Specific Activity | Blood Non-hemolyzed | pH | Protein | Uro-binogen | Nitrate | Leukocytes |
|---|---|---|---|---|---|---|---|---|---|---|

The analyte levels in the table are indicated as follows: (−) negative; (0) traces; (+) low; (+ +) intermediate; (+ + +) high. The number following the parenthesis indicates the number of rats tested.

No significant differences were detected.

B3. The histopathology of adult rats treated topically with Zephalin dissolved in ointment was investigated. The day following the last application of ointment, the animals were sacrificed and their skins and tissues were removed and fixed in formalin. Tissues were embedded in paraffin and sliced into 6 micron slices. Hematoxylin and Oozin were used for staining. The following tissues were tested: (1) Skin in the area treated; (2) Skin in an untreated area; (3) heart; (4) kidneys; and (5) brain.

The tissues were taken from: (1) Eight out of ten rats treated with 0.0002 mg/g of analgesic fraction; (2) Six out of ten rats treated with 0.001 mg/g of analgesic fraction; and (3) the control of eight rats. All tested rats were chosen randomly.

The results are summarized in Table 4.

TABLE 4

| Tissue treated | Control | Zephalin (mg/Kg body weight) (0.03) | (0.15) |
|---|---|---|---|
| Skin | decrease of 50–90% in hair roots in all rats | decrease of 50–90% in hair roots in all rats | decrease of 50–90% in hair roots in all rats |
| Heart | no change | no change | no change |
| Liver | in 2 livers, a small and local case of neutrophils; in all other 6 no changes were seen | in one rat a chronic inflammatory site; no changes in others | in one rat a chronic inflammatory site |
| Kidney | no change | in one rat sites of expansion; in others, no change | no change |
| Brain | no change | no change | no change |

The conclusion was that no significant histopathological changes were observed between the treated and control groups.

In summary, Zephalin was found to have no significant toxicity.

It will be appreciated by persons skilled in the art that the present invention is not limited to what has been thus far described, but rather the scope of the present invention is limited only by the following claims.

What is claimed is:

1. An isolated and purified fraction of the venom of *Vipera xanthina* wherein the fraction is substantially non-toxic and wherein the fraction has a UV absorbency at a wavelength of 280 nm.

2. The fraction according to claim 1, wherein the fraction has an analgesic effect.

3. The fraction according to claim 1, wherein said *Vipera xanthina* is *Vipera xanthina palestinae*.

4. A method for the preparation of a pharmaceutical composition for use as an analgesic comprising adding the fraction of claim 1 wherein said fraction has an analgesic effect, to a pharmaceutically acceptable carrier or excipient.

5. A pharmaceutical composition for use in an analgesic comprising the fraction of claim 1 and a pharmaceutically acceptable carrier or excipient.

6. A pharmaceutical composition according to claim 5 for topical administration.

7. A pharmaceutical composition according to claim 5 for parenteral administration.

8. A pharmaceutical composition according to claim 5 for the treatment of pain.

9. A pharmaceutical composition according to claim 5 wherein said *Vipera xanthina* is *Vipera xanthina palestinae*.

10. A method for the relief of pain comprising administrating to a subject in need thereof the substantially non-toxic fraction according to claim 1.

11. A method according to claim 10 wherein said fraction has the characteristics of a fraction purified from said venom by ion-exchange chromatography.

12. A method according to claim 10 wherein said fraction is topically administered.

13. A method according to claim 10 wherein said *Vipera xanthina* is *Vipera xanthina palestinae*.

14. A method for isolating the fraction of claim 1 comprising applying whole venom of *Vipera xanthina* to an ion exchange column and eluting the fraction.

15. A method according to claim 14 wherein said column is a Mono Q column.

16. A method according to claim 14 wherein said column is a QAE Sephadex column.

17. A method according to claim 14 wherein said *Vipera xanthina* is *Vipera xanthina palestinae*.

\* \* \* \* \*